United States Patent
Howat et al.

(12) 
(10) Patent No.: US 6,881,707 B2
(45) Date of Patent: Apr. 19, 2005

(54) GLYPHOSATE COMPOSITION

(75) Inventors: Peter Dunlop Howat, Canterbury (AU); Phillip Maxwell Hay, Melton (AU)

(73) Assignee: Nufarm Limited, Laverton North (AU)

( * ) Notice: Subject to any disclaimer, the term of this patent is extended or adjusted under 35 U.S.C. 154(b) by 0 days.

(21) Appl. No.: 10/770,378

(22) Filed: Feb. 2, 2004

(65) Prior Publication Data

US 2004/0192552 A1 Sep. 30, 2004

Related U.S. Application Data

(63) Continuation of application No. PCT/AU02/01016, filed on Jul. 31, 2002.
(60) Provisional application No. 60/338,871, filed on Dec. 7, 2001, and provisional application No. 60/311,658, filed on Aug. 10, 2001.

(30) Foreign Application Priority Data

Aug. 3, 2001 (AU) ............................................. PR6822

(51) Int. Cl.$^7$ ................................................ A01N 57/02
(52) U.S. Cl. ...................................................... 504/206
(58) Field of Search ......................................... 504/206

(56) References Cited

U.S. PATENT DOCUMENTS 6,083,875 A * 7/2000 Sato et al. ................... 504/127
6,121,199 A 9/2000 Berger et al.

FOREIGN PATENT DOCUMENTS

| JP | 2001-278711 | 10/2001 |
| WO | WO 92/11764 | 7/1992 |
| WO | WO 99/21424 | 5/1999 |
| WO | WO 00/30451 | 6/2000 |
| WO | WO 01/89302 | 11/2001 |

* cited by examiner

*Primary Examiner*—S. Mark Clardy
(74) *Attorney, Agent, or Firm*—Nixon Peabody LLP

(57) ABSTRACT

The invention provides a glyphosate composition comprising a mixture of salts of glyphosate comprising each of potassium and isopropylammonium salts.

25 Claims, No Drawings

GLYPHOSATE COMPOSITION

This application under 35 U.S.C. § 111 is a continuation of PCT/AU02/01016, filed Jul. 31, 2002, which claims priority benefit of Australian Patent Application No. PR6822, filed Aug. 3, 2001, U.S. Provisional Patent Application Ser. No. 60/311,658, filed Aug. 10, 2001, and U.S. Provisional Patent Application Ser. No. 60/338,871, filed Dec. 7, 2001. The above-identified PCT application is hereby incorporated by reference in its entirety.

FIELD OF THE INVENTION

This invention relates to compositions used to control weeds, and in particular relates to compositions comprising N-phosphonomethylglycine, commonly known as glyphosate. More particularly the invention relates to compositions comprising salts of glyphosate, and to methods for controlling weeds using these formulations.

BACKGROUND

Glyphosate in acid form is relatively water-insoluble, and in order to achieve significant water solubility, glyphosate has generally been formulated as a salt.

Significant tonnages of formulations comprising glyphosate salts are applied throughout the world each year in a wide range of cropping situations and other situations calling for the control of unwanted foliage. The achievement of greater herbicidal efficacy is of great interest because it provides the option of more effective weed control or more efficient use of the active ingredient.

A wide variety of glyphosate salts have been described for example

Franz in U.S. Pat. No. 4,147,719 describes mono or di salts of glyphosate with alkaline metals, alkaline earth metals, ammonium or organic ammonium cations.

Teixeira in WO 8704712 describes dry particulate sodium and potassium salts of glyphosate.

Magin et al in U.S. Pat. No. 5,710,104 describes amine, alkali metal, alkylsulfonium alkylphosphonium, sulfonylamine and aminoguanidine salts of glyphosate.

Broadhurst et al in U.S. Pat. No. 4,431,594 describes sulfonium and sulfoxonium salts of glyphosate as well as phosphonium and substituted ammonium salts.

Jeffrey in DD218366 describes the trisodium salt of glyphosate.

Large in U.S. Pat. No. 4437874 describes tri-mixed alkylsulfonium salts of N-phosphonomethyl glycine.

Large in WO 8303608 describes tetrasubstituted ammonium salts of glyphosate.

Large in EP73574 describes phosphonium salts of glyphosate.

Prisbylla in EP115176 describes stannic salts of glyphosate.

Prisbylla in EP124351 describes mixed long-chain alkylammonium salts of glyphosate.

Gaughan in EP 369076 describes trisubstitued sulfonium and sulfoxonium salts of glyphosate.

Bakel in EP103055 describes isothiouronium diisothiouronium and diguanidinium salts of glyphosate.

The glyphosate salts described above generally comprise a particular cation which is present in a mole ratio of at least 0.9:1 with glyphosate.

Commercially available formulations of glyphosate salts include the "Accord", "Roundup", "Roundup Ultra" and "Roundup Xtra" brands of Monsanto Company. These formulations contain glyphosate as the isopropylammonium salt. Monsanto's Roundup Geoforce brand contains glyphosate sodium salt and Roundup Dry contains glyphosate ammonium salt. The "Touchdown" brand of Zeneca, contains glyphosate trimethyl sulfonium salt.

The above commercial formulations of glyphosate all comprise particular low-molecular weight salt cations (generally of molecular weight less than 300) and a key criterion for selecting the salt in such a formulation is the capacity to achieve high loading levels of glyphosate (acid equivalent) in the formulation.

The herbicidal activity of glyphosate salts can be enhanced by adding a certain quantity of amphiphilic agents (including amphiphilic salts) to the formulation. According to Bryson et al in WO 2000032045, amphiphilic materials (including surfactants) can enhance the activity of a formulation comprising glyphosate salts by

- decreasing the spray drop size and thereby minimizing rebound from a foliar surface
- increasing the adhesion between a spray droplet and a foliar surface
- reducing run-off of spray drops from a foliar surface
- increasing the area of contact between a spray drop and a foliar surface and
- enhancing the penetration of glyphosate from the droplet through the cuticle to reach internal leaf tissue.

Amphiphilic agents may be identified by virtue of their capacity to cause one or more of the following phenomena:
- formulation of micellar aggregates, at concentrations above the critical micellar concentration (CMC)
- reduction of the contact angle between water and a leaf surface
- reduction of the surface tension of an aqueous phase
- stabilization of dispersed oily droplets in the aqueous phase
- reduction of spray drop size.

Amphiphilic agents which have been claimed to enhance the herbicidal efficacy of formulations comprising glyphosate salts include the following:
- quaternary ammonium surfactant;
- etheramine surfactants;
- alkylether and amine surfactant combinations;
- acetylenic diol and alkyl(poly)glycoside surfactant combinations;
- lipophilic fatty amine ethoxylate surfactants;
- alkoxylated amine surfactants;
- alkyl polyglycoside agents;
- secondary or tertiary alcohol surfactants;
- silicone copolymer wetting agents and trialkylamine oxide or quaternary amine or trialkylbetaine surfactant combinations;
- sorbitan fatty acid ester and amine, quaternary ammonium or alkylglycoside surfactant combinations;
- surfactants derived from alkanethiols;
- polyoxyalkylene trisiloxane surfactants;
- super-wetting agents such as silicone-based and fluorocarbon-based surfactants;
- supra-molecular aggregates formed by one or more amphiphilic salts having a glyphosate anion and cations derived by protonation of one or more polyamines or polyamine derivatives, each having at least two nitrogen-containing groups and a $C_6$–$C_{30}$ hydrocarbyl or acyl group;

supra-molecular aggregates comprising one or more amphiphilic salts having a glyphosate anion and cation derived by protonation of secondary or tertiary oily amines;

alkoxylated primary alcohol surfactants;

alkyl polysaccharide derivates;

alkyl polyglycoside and ethoxylated alcohol combinations;

alkylglucosides;

surfactants comprising polyhydroxyhydrocarbyl and amine functionality;

alkylglycoside and alkoxylated alkylamine surfactant combinations;

alkyldiamine tetraalkoxylate surfactants;

succinic acid derivatives;

alkoxylated amido amines;

sugar glycerides such as rapeseed oil sugar glyceride;

diamine surfactants;

widely-bridged alcohol polyethoxylates;

water-soluble long-chain hydrocarbyl dimethylamine oxides and quaternary ammonium halide combinations;

hydroxyalkylammonium adjuvants;

polyether diamine surfactants;

cationic, anionic, nonionic or zwitterionic silicone adjuvants;

organosilicone surfactants and diphenyl oxide sulfonate surfactant combinations;

a range of ether phosphate adjuvants;

phosphourous surfactant adjuvants;

polyglycerol and polyglycerol derivatives;

$C_8$–$C_{22}$ sarcosinate or sarcosinate salts;

ethoxylated vegetable oils;

polyethoxylated dialkylamine surfactants;

$C_{10}$–$C_{18}$ alkylpolyglycol ether sulfates; and salts of fatty acids.

Non-amphiphilic additives have also been claimed to enhance the bioefficacy of glyphosate, for example Toussaint (EP498145) has described the use of an inorganic ammonium salt, preferably ammonium sulphate;

Hay (AU674464) has described the use of an alkyl-substituted ammonium sulfate;

Chamberlain (US5529975) has described the use of polyacrylamide;

Amakasa (JP2000026209) has described the use of ethanol;

Hioki (WO9701281) has described the use of oxalic acid, and lower molecular weight salts thereof.

SUMMARY OF THE INVENTION

We have now found that the bioefficacy of a glyphosate composition can be significantly improved by using specific combinations of low molecular weight non-amphiphilic cations. Examples of low molecular weight non-amphiphilic cations include but are not limited to cations. such as isopropylammonium, potassium, sodium, ammonium, trimethylsulfonium and monoethanolammonium cations.

In accordance with the invention, we provide a glyphosate composition comprising potassium cations and either isopropylammonium cations or monoethanolammonium cations or both. The composition may comprise other cations such as selected from the group consisting of ammonium, sodium, trimethylsulfonium and mixtures thereof.

In glyphosate compositions containing water, the potassium cations isopropylammonium cations, monoethanolammonium cations and optionally other low molecular weight non-amphiphilic cations act as counter-ions to glyphosate anion.

In one particularly preferred embodiment, the glyphosate composition comprises potassium and isopropylammonium cations and optionally other cations, and the mole ratio of isopropylammonium to potassium cations is less than 30:1 and greater than 1:10, more preferably less than 15:1 and greater than 1:2.

In an alternative embodiment, though less preferred, the glyphosate composition comprises potassium and monoethanolammonium cations, and the mole ratio of monoethanolammonium to potassium cations is less than 30:1 and greater than 1:10, more preferably less than 15:1 and greater than 1:2.

In one of the most preferred embodiments of the invention, the glyphosate composition comprises potassium, monoethanolammonium and isopropylammonium cations, and the mole ratio of isopropylammonium to potassium cations is in the range of from 30:1 to 1:10, and the mole ratio of monoethanolammonium to potassium cations in the range of 30:1 to 1:10. More preferably the mole ratio of isopropylammonium to potassium cations is in the range of 10:1 to 1:5, and the mole ratio of monoethanolammonium to potassium cations in the range of from 10:1 to 1:5.

In this embodiment the glyphosate compositions preferably comprises potassium, monoethanolammonium and isopropylammonium cations in the mole ratio of isopropylammonium cations to the sum of potassium, monoethanolammonium and isopropylammonium cations in the range 50:100 to 95:100. Preferably, the mole ratio of monoethanolammonium to potassium cations in the above formulation is in the range 1:2 to 7:1.

A particularly preferred glyphosate composition comprises isopropylammonium, monoethanolammonium and potassium cations in the ratio 68:16:16.

The glyphosate composition of the invention may and preferably will contain a surfactant. Examples of preferred surfactants for use with the glyphosate composition may be selected from the group consisting of:

etheramine surfactants having the representative chemical structure (a)

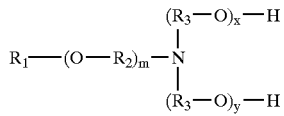

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$–$C_4$ alkylene, $R_3$ groups are independently $C_1$–$C_4$ alkylene, and x and y are average numbers such that x+y is in the range from 2 to about 60; or (b)

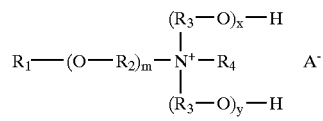

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$–$C_4$ alkylene, $R_3$ groups are independently $C_1$–$C_4$ alkylene, $R_4$ is $C_1$–$C_4$ alkyl, x and y are average numbers such that x+y is in the range from 0 to about 60 and $A^-$ is an agriculturally acceptable anion; or (c)

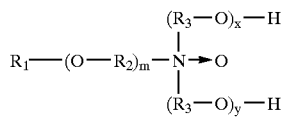

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$–$C_4$ alkylene, $R_3$ groups are independently $C_1$–$C_4$ alkylene and x and y are average numbers such that x+y is in the range from 2 to about 60.

The glyphosate composition of the invention may be in the form of a water soluble granule or powder, a water dispersible granule or powder, an aqueous solution or other suitable form.

In one embodiment the composition is in the form of an aqueous solution containing in the range of from 0.5 to 600 g/l glyphosate mixed salt (based on glyphosate acid) and preferably from 5.0 to 600 g/l.

In a particularly preferred embodiment of the invention the number of moles of potassium cation in the composition will be at least 1% based on the number of moles of glyphosate (determined as glyphosate acid). More preferably the amount of potassium is in the range of from 3 to 50 mole percent of total glyphosate. The amount of potassium will preferably also constitute at least 3% on a molar basis of the total number of moles of potassium, monoisopropylammonium and isopropylammonium and preferably from 3 to 50 mole percent.

In an alternative aspect the invention provides a glyphosate composition in solid particulate form. The particles of the composition may be fine particles such as powder or alternatively the compositions may be in granular or prill form.

Solid powder or granular free-flowing glyphosate compositions may include a surfactant such as at least one surfactant selected from the group consisting of
  (a) ethoxylated aliphatic alcohols or acids having at least 10 moles of ethylene oxide per mole of acid or alcohol and 8 to 24 carbon atoms in the acid or alcohol chain;
  (b) block or random co-polymers of ethylene oxide and propylene oxide; and
  (c) block or random copolymers of ethylene oxide and propylene oxide based on aliphatic alcohols having 4 to 18 carbon atoms.

These solid compositions may include urea, other fertilizers, such as diammonium phosphate; acidifying agents, such as anionic phosphate esters of the formula $ROP(O)(OH)_2$ wherein R is alkyl, alkylaryl, alkoxylated alkyl, or alkoxylated alkylaryl; and/or sticking agents, such as fatty acids, fatty acid esters or alkoxylated novolac resins.

In one embodiment the adjuvant includes urea and the composition is eutectic. The adducts may be formed by mixing and heating a composition containing urea to form a uniform liquid melt and then cooling the adduct into a solid, free-flowing powder. In this embodiment the solid free flowing adjuvants may be included in the composition prior to forming the melt or dry blended with glyphosate component of the composition.

The composition may also be formed into water soluble or dispersible granules by applying the surfactant preferably by spraying into a mixer containing a solid flowable mixture including mixed salts of glyphosate and optionally other additives such as fertilizers, fillers or the like and forming granules by extrusion, pan granulation or other suitable method.

The solid adjuvant systems will most preferably use non-ionic surfactants. These surfactants may be liquids or waxy solids. Adsorbents, such as clays or silicas, may be employed but it may be desirable to avoid such insoluble additives where spray equipment is to be used as they may clog spray lines and nozzles or increase nozzle wear.

Details of suitable solid adjuvants for use in the glyphosate composition of the invention are described in the specification and examples of Canadian Patent No. 2093377 the contents of which are herein incorporated by reference.

In a further aspect the invention provides a method of preparation of the above described glyphosate composition. The glyphosate composition may be prepared by mixing salts of glyphosate such as the potassium and one or both of the isopropylamine and ethanolammonium salts in solid form or aqueous solution.

Alternatively one or more cations may be provided by combining a base with glyphosate wherein the base provides one or more of the cations in aqueous slurry of glyphosate (preferably in the form of glyphosate acid).

In one embodiment the method of the invention comprises forming a slurry of glyphosate (preferably as glyphosate acid) and adding separately or in admixture bases which form the potassium and one or both of monoethanolammonium and isopropylammonium cations on addition to the slurry. The base may for example contain potassium hydroxide and optionally one or both of isopropylamine and monoethanolamine.

In a further aspect the invention provides a method of forming a solid glyphosate composition comprising forming a slurry of glyphosate; combining the slurry with potassium hydroxide and one or both of monoisopropylamine and monoethanolamine to form a composition comprising the mixed salts of glyphosate.

The resulting glyphosate mixed salt composition may in many cases be isolated by filtration for example from an aqueous/alcohol mixture. It may be formulated with suitable surfactants and optionally other additives such as urea, fertilizers, fillers and ammonium sulphate.

In a further aspect the invention provides a method of preparing a glyphosate composition comprising forming a mixture of glyphosate salts including at least the potassium salts and at least one of ethanolammonium and isopropylammonium salts of glyphosate.

In a further aspect the invention provides a method of controlling weeds comprising applying to the weeds a composition of glyphosate as hereinbefore described. The compositions of the invention generally exhibit synergy. Thus the mixed salts of the invention typically provide a level of activity in controlling weeds which would not be expected from the additive effect of individual salt.

The mixed salt glyphosate formulations of this invention may further comprise amphiphilic adjuvants known to the art, for example adjuvants described previously.

The invention will now be described with reference to the following examples. It is to be understood that the examples are provided by way of illustration of the invention and that they are in no way limiting to the scope of the invention.

EXAMPLES

Example 1

Preparation of Glyphosate Formulations with a Range of Non-Amphiphilic Cations 1.1 Formulation CT (Comparative Formulation)
Formulation CT consisted of
- 43.37 parts glyphosate technical comprising 85% glyphosate, 12% water and 3% impurities; and
- 13.53 parts isopropylamine; and
- 11.06 parts polyethyleneglycol 20 tallowamine blend, sold by Huntsman Chemicals of Melbourne, Australia; and
- 30.54 parts water The non-amphiphilic cations in the above formulation were IPA cations and the mole ratio of IPA cations to other non-amphiphilic cations was 100:0

1.2 Formulation 635
Formulation 65 consisted of
- 42.05 parts glyphosate technical, comprising 85% glyphosate, 11.6% water, 3.4% impurities; and
- 4.99 parts isopropylamine; and
- 7.91 parts potassium hydroxide [90% w/w]; and
- 9.53 parts SURFONIC AGM 550, an etheramine surfactant sold by Huntsman Australia; and
- 35.27 parts water 1.3 Formulation 625 (Comparative Example)
Formulation 625 consisted of
- 43.17 parts of glyphosate technical, comprising 85% glyphosate, 12% water and 3% impurities; and
- 13.57 parts isopropylamine; and
- 9.79 parts TERWET 1215 surfactant, an aqueous blend of alkypolysaccharide and alkoxylated alkylether polyamine sold by Huntsman Corporation, Australia Pty Ltd; and
- 32.77 parts water The non-amphiphilic cations in the formulation were IPA cations and the mole ratio for IPA cations to other non-amphiphilic cations was 100:0

1.4 Formulation 621
Formulation 621 consisted of
- 42.05 parts glyphosate technical, comprising 85% glyphosate, 11.6% water and 3.4% impurities; and
- 4.99 parts isopropylamine; and
- 7.91 parts of 90% w/w hydroxide; and
- 9.53 parts TERWET 1215 surfactant; and
- 36.27 parts water.

The non-amphiphilic cations in the above formulation were IPA cations and K cations, and the relative mole ratio of these cations was 40:60

1.5 Formulation 620
Formulation 620 consisted of
- 41.99 parts of glyphosate technical, comprising 85% glyphosate, 11.6% water and 3.4% impurities; and
- 7.47 parts isopropylamine; and
- 5.26 parts 90% w/w potassium hydroxide; and
- 9.52 parts TERWET 1215 surfactant; and
- 35.6 parts water The non-amphiphilic cations in the above formulation were IPA and K cations, and the relative mole ratio of these cations was 60:40

1.6 Formulation 627 (Comparative Example)
Formulation 627 consisted of
- 42.15 parts glyphosate technical, comprising 85% glyphosate, 11.6% water and 3.4% impurities; and
- 12.94 parts ethanolamine; and
- 9.55 parts SURFONIC AGM 550 surfactant; and
- 35.35 parts water.

The non-amphiphilic cations in the above formulation were MEA cations, and the relative mole ratio s of these cations to other non-amphiphilic cations was 100:0

1.7 Formulation 629
Formulation 629 consisted of
- 47.77 parts glyphosate technical, comprising 85% glyphosate, 11.6% water and 3.4% impurities; and
- 13.2 parts ethanolamine; and
- 1.50 parts 90% w/w potassium hydroxide; and
- 7.96 parts TERWET 1215 surfactant; and
- 29.57 parts water The non-amphiphilic cations in the above formulations were MEA cations and K cations, and the relative mole ratio of these cations was 90:10

1.8 Formulation 641
Formulation 641 consisted of
- 47.6 parts glyphosate technical, comprising 85% glyphosate, 11.6% water, 3.4% impurities; and
- 7.33 parts isopropylamine; and
- 5.65 parts ethanolamine (EA); and
- 1.19 parts of 90% w/w potassium hydroxide; and
- 7.93 parts of surfactant SURFONIC AGM 550 (SURFONIC EA); and
- 28.71 parts water 1.9 Formulation 642
Formulation 642 consisted of
- 47.6 parts glyphosate technical, comprising 85% glyphosate, 11.6% water, 3.4% impurities; and
- 7.33 parts isopropylamine; and
- 5.65 parts ethanolamine(EA); and
- 1.19 parts of 90% w/w potassium hydroxide; and
- 7.93 parts of surfactant, TERWET 1215; and
- 28.71 parts water The non-amphiphilic cations in the above formulations were K, EA, IPA and the relative mole ratios of these cations was 8:40:52

1.10 Formulation 521 (Comparative Example)
Formulation 521 consisted of
- 32.78 parts glyphosate technical material comprising 85% glyphosate, 3% impurities and 12% water
- 10.22 parts isopropylamine; and
- 10.13 parts TERWET 1215 surfactant
- 45.73 parts water The non-amphiphilic cations in the above formulations were IPA cations and the mole ratio of IPA cations to other non-amphiphilic cations was 100:0

Example 2

1.11 Solid Formulation

A solid formulation may be prepared by combining technical glyphosate in a slurry with potassium hydroxide, ethanolamine and isopropylamine in a molar ratio of 8:40:52.

The resulting product was filtered and dried.

a) A mixed salt formulation may be added to a solid adjuvant containing:

| | Wt |
|---|---|
| polyoxyethylene (12) tridecyl alcohol | 50% |
| urea | 48.0% |
| water | 2% |

The components may be melted at about 120° C. and stirred to form a liquid melt which may be sprayed into a cooling tower or extruded to form prills or granules.

b) A granular composition may also be prepared by applying a surfactant solution to a flowable powder containing the glyphosate mixed salts and extruding the composition to form pellets and drying the pellets to form granules of less than 15% by weight water content.

Example 3

Bioefficacy Results for Formulations 621 and 625 described in Example 1.

Plants

Annual ryegrass (*Lolium rigidum*) seeds (3/pot) were sown at 5mm depth in 10cm diameter pots filled with potting mix (AS 3743) that had been amended with macro and micro nutrients to ensure optimal growth. One week after seedling emergence, seedlings were thinned for uniform size to one seedling per pot. Plants were grown in a temperature controlled greenhouse (14° C.–25° C.) for 16 days then outdoors for 4 days prior to spray application to simulate field conditions (3½ to 4 leaf stage). After the application of herbicides the pots were returned to the greenhouse for an additional 15 days before plants were assessed for fresh weight.

Herbicide Application

Herbicide formulations were applied using an enclosed laboratory track-sprayer fitted with three 110° flat fan nozzles (Spraying Systems Tee Jet 11001) spaced at 50 cm intervals across the boom. The boom spray moved along a fixed track at 6 km h$^{-1}$, sprayed at a water volume of 64 L ha$^{-1}$ with a pressure of 200 Kpa. Eight replicate treatments were sprayed per rate. Application rates of 35, 70 and 140 g/ha were used. Results (g/plant) were averaged across all application rates.

Two trials were conduced using the above protocol.

| | Trial 2.1 Results | |
|---|---|---|
| Formulation | IPA:K mole ratio | Fresh weight av gram/plant |
| Unsprayed control | — | 0.798 |
| CT | 100:0 | 0.332 |
| 635 | 40:60 | 0.214 |

| | Trial 2.2 Results | |
|---|---|---|
| Formulation | IPA:K | Fresh weight av gram/plant |
| Unsprayed control | — | 0.693 |
| CT | 100:0 | 0.469 |
| 625 | 100:0 | 0.419 |
| 621 | 40:60 | 0.362 |

Example 4

Bioefficacy Results for Formulation 642

The experimental protocol was as for example 2.

| | Mole ratio IPA:MEA:K | Fresh weight av g/plant |
|---|---|---|
| Unsprayed control | | 0.80 |
| CT* | 100:0:0 | 0.33 |
| 641 | 52:40:8 | 0.276 |
| 642 | 52:40:8 | 0.227 |

CT*: Monsanto IPA glyphosate

Example 5.1

Spray solutions were prepared by combining aqueous stock solutions of glyphosate salts (all at 450 g/L glyphosate acid equivalent) in the proportions shown in Table 5.11, and adding the resultant solution to water together with TERWET 1215 (a surfactant sold by Huntsman Australia comprising an aqueous blend of alkyl polysaccharides and alkoxylated alkyl ether polyamines), to represent the application of a formulation containing 450 g/L glyphosate acid equivalent and 120 g/L TERWET 1215 to test plants at both 70 g/ha glyphosate acid and 140 g/ha glyphosate acid equivalent at 64 L/ha water volume.

Annual ryegrass (*Lolium rigidum*) seeds (3/pot) were sown at 5 mm depth in 10 cm diameter pots filled with potting mix. One week after seedling emergence, seedlings were thinned for uniform size to one or two seedling per pot. For efficacy studies, plants were grown in a temperature controlled greenhouse (14–25° C.) for 160 days then outdoors for 4 days prior to spray application to simulate filed conditions (3–4 leaf stage).

Herbicide formulations were applied at 64 liters/ha using an enclosed laboratory track-sprayer fitted with three 110° flat fan nozzles (TeeJet 11001; 200 kPa). After the application of treatments, pots were returned to the greenhouse for an additional 15 days before plants were assessed for fresh weight. Each spray treatment was replicated eight times.

The mean fresh weight of each spray treatment was calculated. For each salt mixture treatment a predicted fresh weight was calculated from the weighted average of the individual salt fresh weight mean value. Treatments where the observed fresh weight of the mixed salt treatment is lower than the corresponding predicted value calculated from the weighted average is considered to show a synergistic effect. The synergy factor was calculated as follows: synergy factor =100% times (predicted fresh weight minus actual fresh weight) divided by actual fresh weight. Treatments where the observed fresh weight of the mixed salt treatment is higher than the corresponding predicted value calculated from the weighted average is considered to show an antagonistic effect.

TABLE 5.11

| | | | | ARG | | | | | |
|---|---|---|---|---|---|---|---|---|---|
| | Mono | mono | | Fresh weight, g | | Predicted value | | Synergy factor | |
| | isopropylamine | ethanolamine | potassium | 70 | 140 | 70 pred | 140 pred | 70 | 140 |
| 1 | 1 | 0 | 0 | 0.394375 | 0.381 | | | | |
| 2 | 0 | 1 | 0 | 0.342375 | 0.279 | | | | |
| 3 | 0 | 0 | 1 | 0.35475 | 0.286 | | | | |
| 12 | ½ | ½ | 0 | 0.368875 | 0.31525 | 0.368375 | 0.33 | −0.14 | 4.68 |
| 13 | ½ | 0 | ½ | 0.2975 | 0.239125 | 0.374563 | 0.3335 | 25.90 | 39.47 |
| 23 | 0 | ½ | ½ | 0.349625 | 0.179875 | 0.348563 | 0.2825 | −0.30 | 57.05 |
| 123 | ⅓ | ⅓ | ⅓ | 0.35 | 0.18925 | 0.363833 | 0.315333 | 3.95 | 66.62 |
| 1123 | ⅔ | ⅙ | ⅙ | 0.2965 | 0.179625 | 0.379104 | 0.359625 | 27.86 | 100.21 |
| 1223 | ⅙ | ⅔ | ⅙ | 0.3225 | 0.21475 | 0.353104 | 0.297167 | 9.49 | 38.38 |
| 1233 | ⅙ | ⅙ | ⅔ | 0.351 | 0.219375 | 0.359292 | 0.300667 | 2.36 | 37.06 |

Examples 5.2

Spray solutions were prepared by combining aqueous stock solutions of glyphosate salts (all at 450 g/L glyphosate acid equivalent) in the proportions shown in Table 5.11, and adding the resultant solution to water together with TERWET 1215 (a surfactant sold by Huntsman Australia comprising an aqueous blend of alkyl polysaccharides and alkoxylated alkyl ether polyamines), to represent the application of a formulation containing 450 g/L glyphosate acid equivalent and 120 g/L TERWET 1215 to test plants at both 70 g/ha glyphosate acid and 140 g/ha glyphosate acid equivalent at 64 L/ha water volume.

The mean fresh weight for each spray treatment was calculated. For each salt mixture treatment a predicted fresh weight was calculated from the weighted average of the individual salt fresh weight mean value. Treatments where the observed fresh weight of the mixed salt treatment is lower than the corresponding predicted value calculated from the weighted average are considered to show a synergistic effect. The synergy factor was calculated as in example 5.1. Treatments were the observed fresh weight of the mixed salt treatment is higher than the corresponding predicted value calculated from the weighted average are considered to show an antagonistic effect.

TABLE 5.21

| | | | | Oats | | | | | |
|---|---|---|---|---|---|---|---|---|---|
| | mono- | mono- | | | | | | Synergy factor | |
| | isopropylamine | ethanolamine | potassium | 70 | 140 | 70 pred | 140 pred | 70 | 140 |
| 1 | 1 | 0 | 0 | 2.2706 | 1.073143 | | | | |
| 2 | 0 | 1 | 0 | 2.1767 | 0.862 | | | | |
| 3 | 0 | 0 | 1 | 1.6451 | 0.887571 | | | | |
| 12 | ½ | ½ | 0 | 1.6547 | 1.334286 | 2.223643 | 0.967571 | 34.38 | −27.48 |
| 13 | ½ | 0 | ½ | 1.6643 | 0.972143 | 1.957857 | 0.980357 | 17.64 | 0.84 |
| 23 | 0 | ½ | ½ | 1.2657 | 0.964571 | 1.910929 | 0.874786 | 50.98 | −9.31 |
| 123 | ⅓ | ⅓ | ⅓ | 1.4326 | 0.914 | 2.03081 | 0.940905 | 41.76 | 2.94 |
| 1123 | ⅔ | ⅙ | ⅙ | 1.2739 | 0.501 | 2.15069 | 1.133286 | 68.83 | 126.20 |
| 1223 | ⅙ | ⅔ | ⅙ | 1.704 | 0.710143 | 2.103762 | 0.901452 | 23.46 | 26.94 |
| 1233 | ⅙ | ⅙ | ⅔ | 1.0311 | 0.686571 | 1.837976 | 0.914238 | 78.25 | 33.16 |

Oat seeds (3/pot) were sown at 5 mm depth in 10 cm diameter pots filled with potting mix. One week after seedling emergence, seedlings were tinned for uniform size to one or two seedlings per pot. For efficacy studies, plants were grown in a temperature controlled greenhouse (14–25° C.) for 16 days then outdoors for 4 days prior to spray application to simulate field conditions (3–4 leaf stage).

Herbicide formulations were applied at 64 liters/ha using an enclosed laboratory track-sprayer fitted with three 1100 flat fan nozzles (TeeJet 11001; 200 kPa). After the application of treatments, pots were returned to the greenhouse for an additional 15 days before plants were assessed for fresh weight. Each spray treatment was replicated eight times.

Example 5.3

Spray solutions were prepared by combining aqueous stock solutions of glyphosate salts (all at 450 g/L glyphosate acid equivalent) in the proportions shown in Table 5.11, and adding the resultant solution to water together with TERWET 1215 (a surfactant sold by Huntsman Australia comprising an aqueous blend of alkyl polysaccharides and alkoxylated alkyl ether polyamines), to represent the application of a formulation containing 450 g/L glyphosate acid equivalent and 120 g/L TERWET 1215 to test plants at both 70 g/ha glyphosate acid and 140 g/ha glyphosate acid equivalent at 64 L/ha water volume.

Canola seeds (3/pots) were sown at 5 mm depth in 10 cm diameter pots filled with potting mix. One week after seedling emergence, seedlings were thinned for uniform size to or two seedlings per pot. For efficacy studies, plants were grown in a temperature controlled greenhouse (14–25° C.) for 16 days then outdoors for 4 days prior to spray application to simulate field conditions (3–4 leaf stage).

Herbicide formulations were applied at 64 liters/ha using an enclosed laboratory track-sprayer fitted with three 110° flat fan nozzles (TeeJet 11001; 200 kPa). After the application of treatments, pots were retuned to the greenhouse for an additional 15 days before plants were assessed for fresh weight. Each spray treatment was replicated eight times.

The mean fresh weight for each spray treatment was calculated. For each salt mixture treatment a predicted fresh weight was calculated from the weighted average of the individual salt fresh weight mean value. Treatments where the observed fresh weight of the mixed salt treatment is lower than the corresponding predicted value calculated from the weighted average are considered to show a synergistic effect. The synergy factor was calculated as in example 5.1. Treatments where the observed fresh weight of the mixed salt treatment is higher than the corresponding predicted value calculated from the weighted average are considered to show an antagonistic effect.

Example 6.1

Spray solutions were prepared by combining aqueous stock solutions of glyphosate salts (all at 450 g/L glyphosate acid equivalent) in the proportions shown in Table 6.11, and adding the resultant solution to water together with TERWET G3780A (an ethoxylated tallow amine surfactant sold by Huntsman Australia), to represent the application of a formulation containing 450 g/L glyphosate acid equivalent and 120 g/L TERWET G3780A to test plants at both 70 g/ha glyphosate acid and 140 g/ha glyphosate acid equivalent at 64 L/ha water volume.

The spray solutions described above were applied to canola (*Brassica napus*). Canola (*Brassica napus*) seeds (3/pot) were sown at 3 mm depth (covered with washed river sand) in 10 cm diameter pots filled with potting mix. One week after seedling. emergence, seedlings were thinned for uniform size to one or two seedlings per pot. For efficacy studies plants were grown in a temperature controlled greenhouse (14–25° C.) for 16 days then outdoors for 4 day prior to spray application to simulate field conditions (2–3 leaf stage).

Herbicide formulations were applied at 64 liters/ha using an enclosed laboratory track-sprayer fitted with three 110°

TABLE 5.31

Canola

| | mono-isopropylamine | mono-ethanolamine | potassium | 70 | 140 | 70 pred | 140 pred | Synergy factor 70 | 140 |
|---|---|---|---|---|---|---|---|---|---|
| 1 | 1 | 0 | 0 | 3.3845 | 1.730125 | | | | |
| 2 | 0 | 1 | 0 | 2.9405 | 1.286 | | | | |
| 3 | 0 | 0 | 1 | 1.993875 | 0.9455 | | | | |
| 12 | ½ | ½ | 0 | 4.129125 | 1.890125 | 3.1625 | 1.508063 | −23.41 | −20.21 |
| 13 | ½ | 0 | ½ | 2.672875 | 1.286625 | 2.689188 | 1.337813 | 0.61 | 3.98 |
| 23 | 0 | ½ | ½ | 1.941 | 0.897625 | 2.467188 | 1.11575 | 27.11 | 24.30 |
| 123 | ⅓ | ⅓ | ⅓ | 1.792286 | 1.005125 | 2.772958 | 1.320542 | 54.72 | 31.38 |
| 1123 | ⅔ | ⅙ | ⅙ | 1.66075 | 1.1905 | 3.078729 | 1.700063 | 85.38 | 42.80 |
| 1223 | ⅙ | ⅔ | ⅙ | 3.398375 | 0.9765 | 2.856729 | 1.303271 | −15.94 | 33.46 |
| 1233 | ⅙ | ⅙ | ⅔ | 1.715375 | 1.05925 | 2.383417 | 1.133021 | 38.94 | 6.96 |

The data from tables 5.11, 5.21 and 5.31 are consolidated in a synergy chart below. All synergy factor results of less than 10% are set at zero in order to highlight the significant results.

| Formulation Label | Ryegrass ARG 70 | Ryegrass ARG140 | Oats 70 | Oats 140 | Canola 70 | Canola 140 |
|---|---|---|---|---|---|---|
| 1 | | | | | | |
| 2 | | | | | | |
| 3 | | | | | | |
| 12 | 0 | 0 | 34 | −27 | −23 | −20 |
| 13 | 26 | 39 | 18 | 0 | 0 | 0 |
| 23 | 0 | 57 | 51 | 0 | 27 | 24 |
| 123 | 0 | 67 | 42 | 0 | 54 | 31 |
| 1123 | 28 | 100 | 69 | 127 | 85 | 42 |
| 1223 | 0 | 38 | 23 | 27 | −16 | 33 |
| 1233 | 0 | 37 | 78 | 33 | 39 | 0 | flat fan nozzles (TeeJet 11001; 200 kPa). After the application of treatments, pots were returned to the greenhouse for an additional 14 days before plants were assessed for fresh weight. Each spray treatment was replicated eight times.

The mean fresh weight for each spray treatment was calculated. For each salt mixture treatment a predicted fresh weight was calculated from the weighted average of the individual salt fresh weight mean value. Treatments where the observed fresh weight of the mixed salt treatment is lower than the corresponding predicted value calculated from the weighted average are considered to show a synergistic effect. The synergy factor was calculated as in example 5.1. Treatments were the observed fresh weight of the mixed salt treatment is higher than the corresponding predicted value calculated from the weighted average are considered to show an antagonistic effect.

TABLE 6.11

Results and data analysis Example 6.1 on canola (*Brassica napus*)

| Fractional salt composition | | | Observed fresh wt, g | | Predicted fresh wt, g | | Synergy factor | |
|---|---|---|---|---|---|---|---|---|
| mono-isopropylamine | mono-ethanolamine | potassium | 70 g/ha | 140 g/ha | 70 g/ha | 140 g/ha | 70 g/ha | 140 g/ha |
| 1 | | | 3.23 | 0.12 | | | | |
| | 1 | | 1.71 | 0.44 | | | | |
| | | 1 | 0.91 | 0.36 | | | | |
| ½ | | ½ | 1.24 | 0.14 | 2.07 | 0.51 | 66.56 | 37.21 |
| ⅔ | ⅙ | ⅙ | 0.77 | 0.18 | 2.59 | 0.44 | 236.46 | 20.30 |

Example 7.1

Spray solutions were prepared by combining aqueous stock solutions (all of 360 g/L glyphosate acid equivalent) in the proportions shown in Table 7.11 and adding the resultant solution to water together with SURFONIC AGM 550 to represent the application of a formulation containing 360 g/L glyphosate acid equivalent and 120 g/L SURFONIC AGM 550 to test plants at both 70 g/ha and/or 140 g/ha glyphosate acid equivalent at 64 L/ha water volume.

The formulation 360 STD was made using glyphosate MIPA salt at 360 g/L acid equivalent and adding the resultant solution to water together with ethoxylated tallow-amine to represent the application of a formulation 360 g/L glyphosate acid equivalent and 120 g/L ethoxylated allow amine to test plants at both 70 g/ha and/or 140 g/ha glyphosate acid equivalent at 64 L/ha water volume.

The bioefficacy results at 14 days after treatment are provided in Table 7.11.

TABLE 7.11

| | | | ARG | | Oats | | Canola | |
|---|---|---|---|---|---|---|---|---|
| MIPA | MEA | Potassium | 70 g/ha | 140 g/ha | 70 g/ha | 140 g/ha | 70 g/ha | 140 g/ha |
| 100 | 0 | 0 | .13 | .07 | 0.63 | 0.4 | 0.8 | 0.6 |
| 0 | 0 | 100 | .1 | .03 | 0.5 | — | 0.7 | 0.55 |
| 17 | 17 | 67 | .08 | .05 | 0.4 | — | — | — |
| 62.5 | 12.5 | 12.5 | .10 | .035 | — | — | — | — |
| 50 | 12.5 | 37.5 | .08 | .05 | 0.5 | — | — | — |
| 50 | 0 | 50 | .07 | .04 | 0.42 | — | — | — |
| 50 | 25 | 25 | — | .045 | — | — | — | — |
| 25 | 50 | 25 | — | .03 | — | — | — | — |
| 62 | 25 | 12.5 | — | — | 0.5 | — | — | 0.5 |
| 17 | 67 | 17 | — | — | 0.35 | — | — | — |
| 25 | 25 | 50 | — | — | 0.5 | — | — | 0.5 |
| 67 | 17 | 17 | — | — | — | — | — | 0.45 |
| 50 | 37 | 12.5 | — | — | — | — | — | — |
| 100* | 0 | 0 | .25 | .1 | 1.5 | — | 1.5 | .85 |

*Formulation 360 STD

Finally, it is understood that various other modifications and/or alterations may be made without departing from the spirit of the present invention as outlined herein.

What is claimed is:

1. A glyphosate composition comprising a mixture of salts of glyphosate comprising each of potassium and isopropylammonium salts.

2. A glyphosate composition according to claim 1 further comprising glyphosate salt formed with monoethanolammonium.

3. A glyphosate composition according to claim 1 wherein the composition contains water.

4. A glyphosate composition according to claim 1 wherein the glyphosate composition further comprises one or more cations selected from the group consisting of ammonium, sodium, trimethylsulfonium and mixtures thereof.

5. A glyphosate composition according to claim 1 wherein the molar ratio of isopropylammonium to potassium cations is in the range of from 30:1 to 1:10.

6. A glyphosate composition according to claim 1 wherein the molar ratio of isopropylammonium to potassium cations is in the range of from 15:1 to 1:2.

7. A glyphosate composition according to claim 2 wherein the molar ratio of monoethanolammonium to potassium cations is in the range of from 30:1 to 1:10.

8. A glyphosate composition according to claim 2 wherein the molar ratio of monoethanolammonium to potassium cations is in the range of from 15:1 to 1:2.

9. A glyphosate composition according to claim 1 comprising potassium, monoethanolammonium and isopropylammonium cations, and wherein the molar ratio of isopropylammonium to potassium cations is from 30:1 to 1:10 and the mole ratio of monoethanolammonium to potassium cations is from 30:1 to 1:10.

10. A glyphosate composition according to claim 1 comprising potassium monoethanolammonium, and isopropylammonium cations, and wherein the molar ratio of isopropylammonium to potassium is from 10:1 to 1:5 and the molar ratio of monoethanolammonium to potassium is in the range of from 10:1 to 1:5.

11. A glyphosate composition according to claim 1 comprising potassium, monoethanolammonium, and isopropylammonium cations, and wherein the ratio of the number of moles of isopropylammonium cations to the sum of (a) the number of moles of potassium cations and (b) the number of moles of isopropylammonium and (c) the number of moles of monoethanolammonium cations is in the range of from 50:100 to 95:100.

12. A glyphosate composition according to claim 11 wherein the mole ratio of monoethanolammonium to potassium cations is in the range of from 1:2 to 7:1.

13. A glyphosate composition according to claim 1 comprising an aqueous solution of glyphosate wherein the glyphosate concentration based on glyphosate acid, is in the range of from 0.5 to 600 g/l.

14. A glyphosate composition according to claim 1 wherein the number of moles of potassium cation in the composition is from 3 to 50% based on the number of moles of glyphosate, determined as glyphosate acid.

15. A glyphosate composition according to claim 1 further comprising a surfactant.

16. A glyphosate composition according to claim 15 wherein the surfactant comprises one or more surfactants selected from the group consisting of:

etheramine surfactants having the representative chemical structure (a)

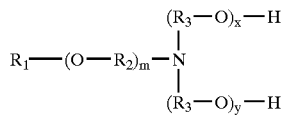

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$–$C_4$ alkylene, $R_3$ groups are independently $C_1$–$C_4$ alkylene, and x and y are average numbers such that x+y is in the range from 2 to about 60; or (b)

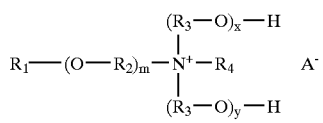

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$–$C_4$ alkylene, $R_3$ groups are independently $C_1$–$C_4$ alkylene, $R_4$ is $C_1$–$C_4$ alkyl, x and y are average numbers such that x+y is in the range from 0 to about 60 and $A^-$ is an agriculturally acceptable anion; or (c)

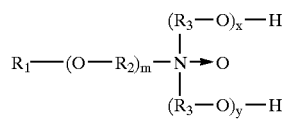

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$–$C_4$ alkylene, $R_3$ groups are independently $C_1$–$C_4$ alkylene and x and y are average numbers such that x+y is in the range from 2 to about 60.

17. A glyphosate composition according to claim 1 in solid particulate form.

18. A glyphosate composition according to claim 17 wherein the composition further comprises a surfactant selected from at least one of the groups consisting of:
  (a) ethoxylated aliphatic alcohols or acids having at least 10 moles of ethylene oxide per mole of acid or alcohol and 8 to 24 carbon atoms in the acid or alcohol chain;
  (b) block or random co-polymers of ethylene oxide and propylene oxide; and
  (c) block or random copolymers of ethylene oxide and propylene oxide based on aliphatic alcohols having 4 to 18 carbon atoms.

19. A glyphosate composition according to claim 17 further comprising one or more adjuvants selected from the group consisting of fertilizers, acidifying agents, and sticking agents.

20. A glyphosate composition according to claim 19 wherein the fertilizer is a urea-based fertilizer, diammonium phosphate, or a combination thereof.

21. A glyphosate composition according to claim 19 wherein the acidifying agent is an anionic phosphate ester of the formula ROP(O)(OH)$_2$ wherein R is alkyl, alkylaryl, alkoxylated alkyl, or alkoxylated alkylaryl; or combinations thereof.

22. A glyphosate composition according to claim 19 wherein the sticking agent is selected from the group of fatty acids, fatty acid esters, alkoxylated novolac resins, and combinations thereof.

23. A method of preparing a glyphosate composition comprising:
  forming a slurry of glyphosate acid and
  mixing the slurry with bases to provide a mixture of salts of glyphosate formed with potassium, isopropylammonium and optionally further comprising monoethanolammonium cations.

24. A method according to claim 23 wherein the glyphosate slurry is mixed with potassium hydroxide and monoisopropylamine and optionally monoethanolamine.

25. A method of controlling weeds comprising applying thereto a glyphosate composition according to claim 1.

* * * * *